(12) United States Patent
Shanley et al.

(10) Patent No.: US 6,764,507 B2
(45) Date of Patent: Jul. 20, 2004

(54) EXPANDABLE MEDICAL DEVICE WITH IMPROVED SPATIAL DISTRIBUTION

(75) Inventors: John F. Shanley, Redwood City, CA (US); Neal L. Eigler, Pacific Palisades, CA (US); Elazer R. Edelman, Brookline, MA (US)

(73) Assignee: Conor Medsystems, Inc., Henlo Park, CA (US)

(*) Notice: Subject to any disclaimer, the term of this patent is extended or adjusted under 35 U.S.C. 154(b) by 0 days.

(21) Appl. No.: 09/948,987

(22) Filed: Sep. 7, 2001

(65) Prior Publication Data

US 2002/0068969 A1 Jun. 6, 2002

Related U.S. Application Data

(63) Continuation-in-part of application No. 09/688,092, filed on Oct. 16, 2000, now abandoned.
(60) Provisional application No. 60/314,360, filed on Aug. 20, 2001, and provisional application No. 60/266,805, filed on Feb. 5, 2001.

(51) Int. Cl.$^7$ ................................................. A61F 2/06
(52) U.S. Cl. ..................................... 623/1.16; 623/1.15
(58) Field of Search ............................ 623/1.15, 1.16, 623/1.17, 1.2, 1.27, 1.3, 1.39, 1.42

(56) References Cited

U.S. PATENT DOCUMENTS

| 3,657,744 A | 4/1972 | Ersek |
| 4,300,244 A | 11/1981 | Bokros |
| 4,531,936 A | 7/1985 | Gordon |
| 4,542,025 A | 9/1985 | Tice et al. |
| 4,580,568 A | 4/1986 | Gianturco |
| 4,650,466 A | 3/1987 | Luther |
| 4,733,665 A | 3/1988 | Palmaz |
| 4,739,762 A | 4/1988 | Palmaz |
| 4,776,337 A | 10/1988 | Palmaz |
| 4,800,882 A | 1/1989 | Gianturco |
| 4,824,436 A | 4/1989 | Wolinsky |
| 4,834,755 A | 5/1989 | Silvestrini et al. |
| 4,955,878 A | 9/1990 | See et al. |

(List continued on next page.)

FOREIGN PATENT DOCUMENTS

| CA | 2234787 | 4/1998 |
| DE | 2002 00 220 | 3/2002 |

(List continued on next page.)

OTHER PUBLICATIONS

U.S. patent application Ser. No. 09/688,092, Shanley, filed Oct. 16, 2000.
U.S. patent application Ser. No. 09/948,989, Shanley, filed Sep. 7, 2001.
Emanelsson, H., et al., *The Jostent Coronary Stent Range*, Ch. 19.
Hwang, C–W, et al. "Physiological Transport forces Govern Drug distribution for Stent–based Delivery".

Primary Examiner—David H. Willse
Assistant Examiner—Javier G. Blanco
(74) Attorney, Agent, or Firm—Cindy A. Lynch

(57) ABSTRACT

An expandable medical device having a plurality of elongated struts, the plurality of elongated struts being joined together by ductile hinges to form a substantially cylindrical device which is expandable from a cylinder having a first diameter to a cylinder having a second diameter. The plurality of struts and ductile hinges are arranged to improve the spatial distribution of the struts which is particularly important when delivering beneficial agents with the struts. The improved strut arrangement expands to a substantially parallelogram shape for improved beneficial agent distribution to the surrounding tissue. A beneficial agent may be loaded into openings within the struts or coated onto the struts for delivery to the tissue.

40 Claims, 6 Drawing Sheets

U.S. PATENT DOCUMENTS

| | | |
|---|---|---|
| 4,957,508 A | 9/1990 | Kaneko et al. |
| 4,960,790 A | 10/1990 | Stella et al. |
| 4,969,458 A | 11/1990 | Wiktor |
| 4,989,601 A | 2/1991 | Marchosky et al. |
| 4,990,155 A | 2/1991 | Wilkoff |
| 4,994,071 A | 2/1991 | MacGregor |
| 5,019,090 A | 5/1991 | Pinchuk |
| 5,049,132 A | 9/1991 | Shaffer et al. |
| 5,053,048 A | 10/1991 | Pinchuk |
| 5,059,166 A | 10/1991 | Fischell et al. |
| 5,059,178 A | 10/1991 | Ya |
| 5,059,211 A | 10/1991 | Stack et al. |
| 5,078,726 A | 1/1992 | Kreamer |
| 5,092,841 A | 3/1992 | Spears |
| 5,102,417 A | 4/1992 | Palmaz |
| 5,157,049 A | 10/1992 | Haugwitz et al. |
| 5,171,217 A | 12/1992 | March et al. |
| 5,171,262 A | 12/1992 | MacGregor |
| 5,176,617 A | 1/1993 | Fischell et al. |
| 5,195,984 A | 3/1993 | Schatz |
| 5,197,978 A | 3/1993 | Hess |
| 5,213,580 A | 5/1993 | Slepian et al. |
| 5,234,456 A | 8/1993 | Silvestrini |
| 5,242,399 A | 9/1993 | Lau et al. |
| 5,286,254 A | 2/1994 | Shapland et al. |
| 5,292,512 A | 3/1994 | Schaefer et al. |
| 5,304,121 A | 4/1994 | Sahatjian |
| 5,314,688 A | 5/1994 | Kauffman et al. |
| 5,342,348 A | 8/1994 | Kaplan |
| 5,342,621 A | 8/1994 | Eury |
| 5,344,426 A | 9/1994 | Lau et al. |
| 5,380,299 A | 1/1995 | Fearnot et al. |
| 5,383,892 A | 1/1995 | Cardon et al. |
| 5,383,928 A | 1/1995 | Scott et al. |
| 5,403,858 A | 4/1995 | Bastard et al. |
| 5,407,683 A | 4/1995 | Shively |
| 5,415,869 A | 5/1995 | Straubinger et al. |
| 5,419,760 A | 5/1995 | Narciso, Jr. |
| 5,439,446 A | 8/1995 | Barry |
| 5,439,686 A | 8/1995 | Desai et al. |
| 5,441,515 A | 8/1995 | Khosravi et al. |
| 5,441,745 A | 8/1995 | Presant et al. |
| 5,443,496 A | 8/1995 | Schwartz et al. |
| 5,443,497 A | 8/1995 | Venbrux |
| 5,443,500 A | 8/1995 | Sigwart |
| 5,447,724 A | 9/1995 | Helmus et al. |
| 5,449,373 A | 9/1995 | Pinchasik et al. |
| 5,449,513 A | 9/1995 | Yokoyama et al. |
| 5,457,113 A | 10/1995 | Cullinan et al. |
| 5,460,817 A | 10/1995 | Langley et al. |
| 5,462,866 A | 10/1995 | Wang |
| 5,464,450 A | 11/1995 | Buscemi et al. |
| 5,464,650 A | 11/1995 | Berg et al. |
| 5,473,055 A | 12/1995 | Mongelli et al. |
| 5,499,373 A | 3/1996 | Richards et al. |
| 5,523,092 A | 6/1996 | Hanson et al. |
| 5,545,210 A | 8/1996 | Hess et al. |
| 5,551,954 A | 9/1996 | Buscemi et al. |
| 5,556,413 A | 9/1996 | Lam |
| 5,575,771 A | 11/1996 | Walinsky |
| 5,578,075 A | 11/1996 | Dayton |
| 5,593,434 A | 1/1997 | Williams |
| 5,607,442 A | 3/1997 | Fischell et al. |
| 5,616,608 A | 4/1997 | Kinsella et al. |
| 5,617,878 A | 4/1997 | Taheri |
| 5,618,299 A | 4/1997 | Khosravi et al. |
| 5,624,411 A | 4/1997 | Tuch |
| 5,628,787 A | 5/1997 | Mayer |
| 5,643,314 A | 7/1997 | Carpenter et al. |
| 5,667,764 A | 9/1997 | Kopia et al. |
| 5,674,278 A | 10/1997 | Boneau |
| 5,697,971 A | 12/1997 | Fischell et al. |
| 5,707,385 A | 1/1998 | Williams |
| 5,713,949 A | 2/1998 | Jayaraman |
| 5,716,981 A | 2/1998 | Hunter et al. |
| 5,725,548 A | 3/1998 | Jayaraman |
| 5,725,549 A | 3/1998 | Lam |
| 5,733,330 A | 3/1998 | Cox |
| 5,733,925 A | 3/1998 | Kunz et al. |
| 5,741,293 A | 4/1998 | Wijay |
| 5,759,192 A | 6/1998 | Saunders |
| 5,766,239 A | 6/1998 | Cox |
| 5,769,883 A | 6/1998 | Buscemi et al. |
| 5,776,181 A * | 7/1998 | Lee et al. .................. 623/1.15 |
| 5,800,507 A | 9/1998 | Schwartz |
| 5,817,152 A | 10/1998 | Birdsall et al. |
| 5,824,045 A | 10/1998 | Alt |
| 5,824,049 A | 10/1998 | Ragheb et al. |
| 5,827,322 A | 10/1998 | Williams |
| 5,837,313 A | 11/1998 | Ding et al. |
| 5,843,117 A | 12/1998 | Alt et al. |
| 5,843,120 A | 12/1998 | Israel et al. |
| 5,843,172 A | 12/1998 | Yan |
| 5,843,175 A | 12/1998 | Frantzen |
| 5,843,741 A | 12/1998 | Wong et al. |
| 5,853,419 A | 12/1998 | Imran |
| 5,855,600 A | 1/1999 | Alt |
| 5,868,781 A | 2/1999 | Killion |
| 5,873,904 A | 2/1999 | Ragheb et al. |
| 5,876,419 A | 3/1999 | Carpenter et al. |
| 5,882,335 A | 3/1999 | Leone et al. |
| 5,886,026 A | 3/1999 | Hunter et al. |
| 5,922,020 A * | 7/1999 | Klein et al. ................. 623/1.15 |
| 5,922,021 A | 7/1999 | Jang |
| 5,957,971 A | 9/1999 | Schwartz |
| 5,964,798 A | 10/1999 | Imran |
| 5,968,092 A | 10/1999 | Buxcemi et al. |
| 5,972,027 A | 10/1999 | Johnson |
| 5,976,182 A | 11/1999 | Cox |
| 5,984,957 A | 11/1999 | Laptewicz, Jr. et al. |
| 6,007,517 A | 12/1999 | Anderson |
| 6,017,363 A | 1/2000 | Hojeibane |
| 6,019,789 A | 2/2000 | Dinh et al. |
| 6,022,371 A | 2/2000 | Killion |
| 6,030,414 A | 2/2000 | Taheri |
| 6,042,606 A | 3/2000 | Frantzen |
| 6,056,722 A | 5/2000 | Jayaraman |
| 6,063,101 A | 5/2000 | Jacobsen et al. |
| 6,071,305 A | 6/2000 | Brown et al. |
| 6,083,258 A | 7/2000 | Yadav |
| 6,087,479 A | 7/2000 | Stamler et al. |
| 6,096,070 A | 8/2000 | Ragheb et al. |
| 6,099,561 A | 8/2000 | Alt |
| 6,120,535 A | 9/2000 | McDonald et al. |
| 6,120,847 A | 9/2000 | Yang et al. |
| 6,153,252 A | 11/2000 | Hossainy et al. |
| 6,156,062 A | 12/2000 | McGuinness |
| 6,159,488 A | 12/2000 | Nagler et al. |
| 6,174,326 B1 | 1/2001 | Kitaoka et al. |
| 6,193,746 B1 | 2/2001 | Strecker |
| 6,206,914 B1 | 3/2001 | Soykan et al. |
| 6,206,915 B1 | 3/2001 | Fagan et al. |
| 6,206,916 B1 | 3/2001 | Furst |
| 6,231,600 B1 | 5/2001 | Zhong |
| 6,240,616 B1 | 6/2001 | Yan |
| 6,241,762 B1 * | 6/2001 | Shanley .................... 623/1.17 |
| 6,245,101 B1 * | 6/2001 | Drasler et al. ............. 623/1.15 |
| 6,249,952 B1 | 6/2001 | Ding |
| 6,273,908 B1 | 8/2001 | Ndondo-Lay |
| 6,273,910 B1 | 8/2001 | Limon |
| 6,273,913 B1 | 8/2001 | Wright et al. |

| | | |
|---|---|---|
| 6,280,411 B1 | 8/2001 | Lennox |
| 6,290,673 B1 | 9/2001 | Shanley |
| 6,293,967 B1 | 9/2001 | Shanley |
| 6,309,414 B1 | 10/2001 | Rolando et al. |
| 6,312,460 B2 | 11/2001 | Drasler et al. |
| 6,395,326 B1 | 5/2002 | Castro et al. |
| 6,451,051 B2 | 9/2002 | Drasler et al. |
| 6,475,237 B2 | 11/2002 | Drasler et al. |
| 6,506,411 B2 | 1/2003 | Hunter et al. |
| 6,506,437 B1 | 1/2003 | Harish et al. |
| 6,544,544 B2 | 4/2003 | Hunter et al. |
| 6,558,733 B1 | 5/2003 | Hossainy et al. |
| 6,599,314 B2 * | 7/2003 | Mathis ................ 623/1.11 |
| 6,605,110 B2 * | 8/2003 | Harrison ............... 623/1.15 |
| 6,663,664 B1 * | 12/2003 | Pacetti ................ 623/1.2 |
| 2001/0000802 A1 | 5/2001 | Soykan et al. |
| 2001/0027340 A1 | 10/2001 | Wright et al. |
| 2001/0034363 A1 | 10/2001 | Li et al. |
| 2001/0044648 A1 | 11/2001 | Wolinsky et al. |
| 2001/0044652 A1 * | 11/2001 | Moore ................ 623/1.16 |
| 2002/0002400 A1 | 1/2002 | Drasler et al. |
| 2002/0005206 A1 | 1/2002 | Falotico et al. |
| 2002/0007209 A1 | 1/2002 | Scheerder et al. |
| 2002/0022876 A1 | 2/2002 | Richter et al. |
| 2002/0038145 A1 * | 3/2002 | Jang ................ 623/1.15 |
| 2002/0072511 A1 | 6/2002 | New et al. |
| 2002/0082679 A1 | 6/2002 | Sirhan et al. |
| 2002/0094985 A1 | 7/2002 | Hermann et al. |
| 2002/0123801 A1 | 9/2002 | Pacetti et al. |
| 2002/0142039 A1 | 10/2002 | Claude |
| 2002/0155212 A1 | 10/2002 | Hossainy |
| 2003/0055487 A1 * | 3/2003 | Calisse ................ 623/1.15 |

FOREIGN PATENT DOCUMENTS

| | | | | |
|---|---|---|---|---|
| EP | 0 335 341 | 10/1989 | | |
| EP | 0 353 341 | 2/1990 | | |
| EP | 0375 520 | 6/1990 | | |
| EP | 0 470 246 | 2/1992 | | |
| EP | 0470 569 | 2/1992 | | |
| EP | 0566 245 | 10/1993 | | |
| EP | 0567 816 | 11/1993 | | |
| EP | 0627 226 | 12/1994 | | |
| EP | 0679 373 | 11/1995 | | |
| EP | 0734 698 | 10/1996 | | |
| EP | 0 747 069 | 12/1996 | | |
| EP | 0 770 401 | 5/1997 | | |
| EP | 0706 376 | 6/1997 | | |
| EP | 0897 700 | 2/1999 | | |
| EP | 0 950 386 | 10/1999 | | |
| EP | 1 118 325 | 7/2001 | | |
| EP | 1 132 058 | 9/2001 | | |
| EP | 1 132 058 A1 * | 9/2001 | ............. | A61F/2/06 |
| EP | 1 172 074 | 1/2002 | | |
| EP | 1 223 305 | 7/2002 | | |
| EP | 1 236 478 | 9/2002 | | |
| FR | 2 764 794 | 12/1998 | | |
| WO | WO 90/13332 | 11/1990 | | |
| WO | WO 91/10424 | 7/1991 | | |
| WO | WO 91/11193 | 8/1991 | | |
| WO | WO 91/12779 | 9/1991 | | |
| WO | WO 92/12717 | 8/1992 | | |
| WO | WO 92/15286 | 9/1992 | | |
| WO | WO 93/06792 | 4/1993 | | |
| WO | WO 94/21308 | 9/1994 | | |
| WO | WO 94/24961 | 11/1994 | | |
| WO | WO 95/03036 | 2/1995 | | |
| WO | WO 95/03795 | 2/1995 | | |
| WO | WO 95/24908 | 9/1995 | | |
| WO | WO 96/03092 | 2/1996 | | |
| WO | WO 96/25176 | 8/1996 | | |
| WO | WO 96/29028 | 9/1996 | | |
| WO | WO 96/32907 | 10/1996 | | |
| WO | WO 97/04721 | 2/1997 | | |
| WO | WO 98/08566 | 3/1998 | | |
| WO | WO 98/18407 | 5/1998 | | |
| WO | WO 98/19628 | 5/1998 | | |
| WO | WO 98/23228 | 6/1998 | | |
| WO | WO 98/23244 | 6/1998 | | |
| WO | WO 98/36784 | 8/1998 | | |
| WO | WO 98/58600 | 12/1998 | | |
| WO | WO 99/15108 | 4/1999 | | |
| WO | WO 99/16386 | 4/1999 | | |
| WO | WO 99/16477 | 4/1999 | | |
| WO | WO 99/44536 A1 * | 9/1999 | ............. | A61F/2/06 |
| WO | WO 99/49928 | 10/1999 | | |
| WO | WO 99/55396 | 11/1999 | | |
| WO | WO 00/10613 | 3/2000 | | |
| WO | WO 00/45744 | 8/2000 | | |
| WO | WO 00/69368 | 11/2000 | | |
| WO | WO 00/71054 | 11/2000 | | |
| WO | WO 01/17577 | 3/2001 | | |
| WO | WO 01/45862 | 6/2001 | | |
| WO | WO 01/49338 | 7/2001 | | |
| WO | WO 01/87376 | 11/2001 | | |
| WO | WO 02/17880 | 3/2002 | | |
| WO | WO 02/26281 | 4/2002 | | |

* cited by examiner

EXPANDABLE MEDICAL DEVICE WITH IMPROVED SPATIAL DISTRIBUTION

CROSS-REFERENCE TO RELATED APPLICATIONS

This application is a continuation-in-part of U.S. application Ser. No. 09/688,092, filed Oct. 16, 2000, now abandoned which is incorporated herein by reference in its entirety. This application also claims priority to U.S. Provisional Application Serial No. 60/266,805, filed Feb. 5, 2001 and to U.S. Provisional Application Serial No. 60/314,360, filed Aug. 20, 2001 which are incorporated herein by reference in their entirety.

BACKGROUND OF THE INVENTION

1. Field of the Invention

The present invention relates to tissue-supporting medical devices, and more particularly to expandable, non-removable devices that are implanted within a bodily lumen of a living animal or human to support the organ and maintain patency, and that have improved spatial distribution for delivery of a beneficial agent to the intervention site.

2. Summary of the Related Art

In the past, permanent or biodegradable devices have been developed for implantation within a body passageway to maintain patency of the passageway. These devices are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Known stent designs include monofilament wire coil stents (U.S. Pat. No. 4,969,458); welded metal cages (U.S. Pat. Nos. 4,733,665 and 4,776,337); and, most prominently, thin-walled metal cylinders with axial slots formed around the circumference (U.S. Pat. Nos. 4,733,665; 4,739,762; and 4,776,337). Known construction materials for use in stents include polymers, organic fabrics and biocompatible metals, such as, stainless steel, gold, silver, tantalum, titanium, and shape memory alloys such as Nitinol.

U.S. Pat. Nos. 4,733,665; 4,739,762; and 4,776,337 disclose expandable and deformable interluminal vascular grafts in the form of thin-walled tubular members with axial slots allowing the members to be expanded radially outwardly into contact with a body passageway. After insertion, the tubular members are mechanically expanded beyond their elastic limit and thus permanently fixed within the body. U.S. Pat. No. 5,545,210 discloses a thin-walled tubular stent geometrically similar to those discussed above, but constructed of a nickel-titanium shape memory alloy ("Nitinol"), which can be permanently fixed within the body without exceeding its elastic limit. All of these stents share a critical design property: in each design, the features that undergo permanent deformation during stent expansion are prismatic, i.e., the cross sections of these features remain constant or change very gradually along their entire active length. These prismatic structures are ideally suited to providing large amounts of elastic deformation before permanent deformation commences, which in turn leads to sub-optimal device performance in important properties including stent expansion force, stent recoil, strut element stability, stent securement on delivery catheters and radiopacity.

U.S. Pat. No. 6,241,762 which is incorporated herein by reference in its entirety, discloses a non-prismatic stent design which remedies the above mentioned performance deficiencies of previous stents. In addition, preferred embodiments of this patent provide a stent with large, non-deforming strut and link elements, which can contain holes without compromising the mechanical properties of the strut or link elements, or the device as a whole. Further, these holes may serve as large, protected reservoirs for delivering various beneficial agents to the device implantation site.

Of the many problems that may be addressed through stent-based local delivery of beneficial agents, one of the most important is restenosis. Restenosis is a major complication that can arise following vascular interventions such as angioplasty and the implantation of stents. Simply defined, restenosis is a wound healing process that reduces the vessel lumen diameter by extracellular matrix deposition and vascular smooth muscle cell proliferation and which may ultimately result in renarrowing or even reocclusion of the lumen. Despite the introduction of improved surgical techniques, devices and pharmaceutical agents, the overall restenosis rate is still reported in the range of 25% to 50% within six to twelve months after an angioplasty procedure. To treat this condition, additional revascularization procedures are frequently required, thereby increasing trauma and risk to the patient.

Several techniques under development to address the problem of restenosis are irradiation of the injury site and the use of conventional stents to deliver a variety of beneficial or pharmaceutical agents to the traumatized vessel lumen. In the latter case, a conventional stent is frequently surface-coated with a beneficial agent (often a drug-impregnated polymer) and implanted at the angioplasty site. Alternatively, an external drug-impregnated polymer sheath is mounted over the stent and co-deployed in the vessel.

While acute outcomes from radiation therapies appeared promising initially, long term beneficial outcomes have been limited to restenosis occurring within a previously implanted stent, so-called 'in-stent' restenosis. Radiation therapies have not been effective for preventing restenosis in de novo lesions. Polymer sheaths that span stent struts have also proven problematic in human clinical trials due to the danger of blocking flow to branch arteries, incomplete apposition of stent struts to arterial walls and other problems. Unacceptably high levels of MACE (Major Adverse Cardiac Events that include death, heart attack, or the need for a repeat angioplasty or coronary artery bypass surgery) have resulted in early termination of clinical trials for sheath covered stents.

Conventional stents with surface coatings of varius beneficial agents, by contrast, have shown promising early results. U.S. Pat. No. 5,716,981, for example, discloses a stent that is surface-coated with a composition comprising a polymer carrier and paclitaxel (a well-known compound that is commonly used in the treatment of cancerous tumors). The patent offers detailed descriptions of methods for coating stent surfaces, such as spraying and dipping, as well as the desired character of the coating itself: it should "coat the stent smoothly and evenly" and "provide a uniform, predictable, prolonged release of the anti-angiogenic factor." Surface coatings, however, can provide little actual control over the release kinetics of beneficial agents. These coatings are necessarily very thin, typically 5 to 8 microns deep. The surface area of the stent, by comparison is very large, so that the entire volume of the beneficial agent has a very short diffusion path to discharge into the surrounding tissue. The resulting cumulative drug release profile is characterized by a large initial burst, followed by a rapid approach to an asymptote, rather than the desired "uniform, prolonged release," or linear release.

Increasing the thickness of the surface coating has the beneficial effects of improving drug release kinetics including the ability to control drug release and to allow increased drug loading. However, the increased coating thickness results in increased overall thickness of the stent wall. This is undesirable for a number of reasons, including increased trauma to the vessel lumen during implantation, reduced flow cross-section of the lumen after implantation and increased vulnerability of the coating to mechanical failure or damage during expansion and implantation. Coating thickness is one of several factors that affect the release kinetics of the beneficial agent, and limitations on thickness thereby limit the range of release rates, durations, and the like that can be achieved.

Recent research described in a paper titled "Physiological Transport Forces Govern Drug Distribution for Stent-Based Delivery" by Chao-Wei Hwang et al. has revealed an important interrelationship between the spatial and temporal drug distribution properties of drug eluting stents, and cellular drug transport mechanisms. In pursuit of enhanced mechanical performance and structural properties stent designs have evolved to more complex geometries with inherent inhomogeneity in the circumferential and longitudinal distribution of stent struts. Examples of this trend are the typical commercially available stents which expand to a roughly diamond or hexagonal shape when deployed in a bodily lumen. Both have been used to deliver a beneficial agent in the form of a surface coating. Studies have shown that lumen tissue portions immediately adjacent to the struts acquire much higher concentrations of drug than more remote tissue portions, such as those located in the middle of the "diamond" shaped strut cells. Significantly, this concentration gradient of drug within the lumen wall remains higher over time for hydrophobic beneficial agents, such as paclitaxel or rapamycin, which have proven to be the most effective anti-proliferatives to date. Because local drug concentrations and gradients are inextricably linked to biological effect, the initial spatial distribution of the beneficial agent sources (the stent struts) is key to efficacy.

U.S. Pat. No. 5,843,120 discloses an expandable device comprising two groups of deformable elements. The first groups comprise a cylindrical arrays of generally parallel struts connected at alternating strut ends, or junctions, which accommodate radial (circumferential) expansion of the device. Even and odd first groups of struts are specified such that odd first groups are shifted circumferentially so as to be "180° degrees out of phase" with even first groups, i.e., with strut junctions of even first groups directly opposed to strut junctions of odd first groups. The second groups of elements are generally flexible bridging elements that connect the junctions of even and odd first groups. This configuration gives rise to the common "diamond" pattern of struts in stent expansion. One frequently used index of the distance of the most distant lumen tissue portions from the nearest drug-eluting element is the "inscribed circle." This is simply the largest circle that can be inscribed in the open cell area bordered by a given set of strut elements, for example, the largest circle that could be inscribed in the diamond pattern cell described above. Smaller inscribed circles, indicating shorter drug diffusion paths and correspondingly lower concentration variations, are more desirable.

A central feature of U.S. Pat. No. 5,843,120 is that the bridging elements (second group elements) are configured to expand along the longitudinal axis of the device to compensate for the longitudinal contraction that occurs in the first groups of struts when the device is expanded radially, so that the device does not undergo overall longitudinal contraction during radial expansion. This property of the device leads to further inhomogeneity in the spatial distribution of the beneficial agent. The bridging elements generally have a substantially smaller width (for flexibility) than the first groups of struts, and have a correspondingly smaller surface area for conveying beneficial agents in the form of coatings. During device expansion the even and odd first groups of struts, with their relatively high surface area, contract longitudinally, further concentrating drug in smaller annular slices of tissue. Conversely, the low surface area bridging elements expand longitudinally during expansion, effectively reducing the amount of beneficial agent deliver at the larger annular slices of tissue adjacent the bridging elements. The net effect of the longitudinally contracting first group of struts and longitudinally expanding bridging elements is to increase tissue concentration variations of the beneficial agent.

It would be desirable to provide a stent structure with smaller inscribed circles and corresponding lower beneficial agent concentration variations. It would also be desirable to provide a stent structure with more even beneficial agent concentration distributions between stent struts and bridging elements.

SUMMARY OF THE INVENTION

In view of the drawbacks of the prior art, it would be advantageous to provide a stent capable of delivering a relatively large volume of a beneficial agent to a traumatized site in a vessel lumen while avoiding the numerous problems associated with surface coatings containing beneficial agents, without increasing the effective wall thickness of the stent, and without adversely impacting the mechanical expansion properties of the stent.

It would further be advantageous to have a tissue supporting device which improves the spatial distribution of beneficial agents in lumen tissue by decreasing the mean and maximum distances between lumen tissue portions and agent-eluting elements of the device, while staying within the desirable range of ratios of device area to lumen tissue area and allowing side branch perfusion.

In accordance with one aspect of the invention, an expandable medical device includes a plurality of elongated struts, the plurality of elongated struts joined together to form a substantially cylindrical device which is expandable from a cylinder having a first diameter to a cylinder having a second diameter, wherein adjacent ones of the plurality of elongated struts are substantially parallel when the cylinder is at the first diameter and the adjacent elongated struts form V-shapes when the cylinder is at the second diameter, and a plurality of pivots joining the plurality of struts together in the substantially cylindrical device, wherein only one pivot interconnects each two adjacent elongated struts and the pivots are each located offset from a line bisecting the V-shapes formed by the elongated struts when the cylinder is at the second diameter.

In accordance with a further aspect of the present invention, an expandable medical device includes a plurality of elongated struts, the plurality of elongated struts joined together to form a substantially cylindrical device which is expandable from a cylinder having a first diameter to a cylinder having a second diameter, wherein adjacent ones of the plurality of elongated struts are substantially parallel when the cylinder is at the first diameter and the adjacent elongated struts form V-shapes when the cylinder is at the second diameter, and a plurality of ductile hinges connecting the plurality of struts together in the substantially cylindrical device, wherein only one ductile hinge interconnects each two adjacent elongated struts and the ductile hinges are each located offset from a line bisecting the V-shapes formed by the elongated struts when the cylinder is at the second diameter, the ductile hinges having a hinge width which is smaller than a strut width such that as the device is expanded from the first diameter to the second diameter the ductile hinges experience plastic deformation while the struts are not plastically deformed.

In accordance with another aspect of the present invention, an expandable medical device includes a plurality of cylindrical members which are expandable from a cylinder having a first diameter to a cylinder having a second diameter, each of the plurality of cylindrical members comprising a plurality of L-shaped struts and a plurality of ductile hinges, wherein each of the plurality of L-shaped struts is joined to an adjacent L-shaped strut by a ductile hinge, and wherein a width of the ductile hinges is smaller than a width of the L-shaped struts such that as the plurality of cylindrical members are expanded from the first diameter to the second diameter the ductile hinges experience plastic deformation while the L-shaped struts are not plastically deformed and a plurality of bridging members connecting the L-shaped struts of adjacent cylindrical members to form an expandable device configured for radial expansion while a longitudinal distance between ends of the plurality of cylindrical members does not increase.

In accordance with an additional aspect of the present invention, an expandable medical device includes a plurality of struts each having a long leg, a short leg connected to the long leg, and a connecting point, wherein the long leg has a length longer than a length of the short leg, a plurality of pivots joining the long leg of one strut to the short leg of an adjacent strut to form a substantially cylindrical device which is expandable from a cylinder having a first diameter to a cylinder having a second diameter, wherein as the substantially cylindrical device is expanded from the first diameter to the second diameter the pivots bend, and a plurality of bridging members connected to the connecting points of struts in one row and to the connecting points of struts in an adjacent row to form an expandable device configured such that a total length of the bridging members remains substantially constant during radial expansion.

In accordance with another aspect of the present invention, an expandable medical device includes a plurality of elongated struts, the plurality of elongated struts joined together by pivoting connections to form a substantially cylindrical device which is expandable from a cylinder having a first diameter to a cylinder having a second diameter, wherein adjacent ones of the plurality of elongated struts are substantially parallel when the cylinder is at the first diameter and the adjacent elongated struts form a plurality of substantially parallelogram shapes when the cylinder is at the second diameter.

In accordance with a further aspect of the present invention, an expandable medical device for delivery of a beneficial agent includes a plurality of elongated struts, the plurality of elongated struts joined together by pivoting connections to form a substantially cylindrical device which is expandable from a cylinder having a first diameter to a cylinder having a second diameter, wherein adjacent ones of the plurality of elongated struts are substantially parallel when the cylinder is at the first diameter and the adjacent elongated struts form a plurality of substantially parallelogram shapes when the cylinder is at the second diameter, and a beneficial agent affixed to the plurality of struts for delivery to tissue.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

Figure 2:
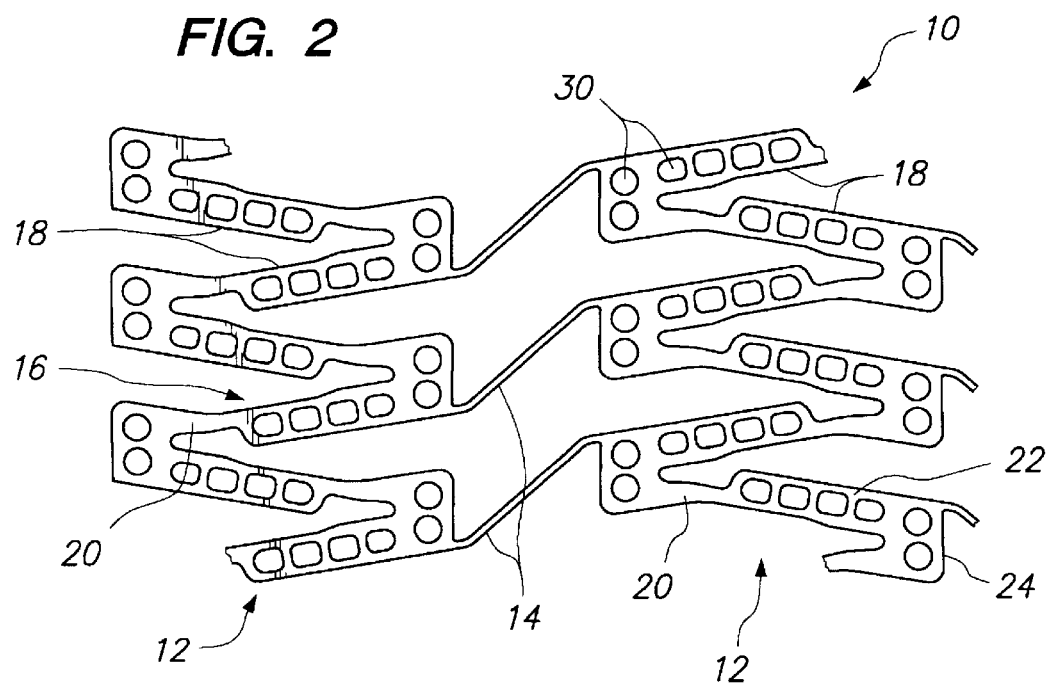
FIG. 2 is an enlarged side view of a portion of tissue-supporting device in accordance with a first preferred embodiment of the present invention.

FIG. 2 illustrates a portion of a cylindrical tissue supporting device 10 according to the present invention which improves the spatial distribution of beneficial agent delivered to tissue by the tissue supporting device. The tissue supporting device 10 includes a strut arrangement which decreases the mean and maximum distances between lumen tissue portions and agent-eluting elements of the devices, while staying within the desirable range of ratios of device area to lumen tissue area and allowing side branch perfusion. The tissue supporting device 10 achieves the improved spatial distribution with a strut arrangement which expands to substantially parallelogram shaped cells. The tissue supporting device 10 is preferably provided with a beneficial agent loaded in a plurality of openings in the device. Alternatively, the beneficial agent for delivery to the lumen tissue may be coated on the device 10.

The tissue supporting device 10 is shown in the Figures in an unrolled flat view of a portion of the device for ease of illustration. The device 10 is preferably cut from a tube of material to form a cylindrical expandable device. The tissue supporting device 10 includes a plurality of sections forming cylindrical tubes 12 connected by bridging elements 14. The bridging elements 14 allow the tissue supporting device to bend axially when passing through the tortuous path of the vasculature to the deployment site and allow the device to bend when necessary to match the curvature of a lumen to be supported. Each of the cylindrical tubes 12 has a plurality of axial slots 16 extending from each end surface of the cylindrical tube toward an opposite end surface.

Formed between the slots 16 is a network of elongated struts 18. Preferably, the elongated struts 18 are L-shaped struts each having a long leg 22 and a short leg 24. Each individual elongated strut 18 is preferably linked to an adjacent strut through reduced sections called ductile hinges 20, one at each end, which act as stress/strain concentration features. The ductile hinges 20 of the struts function as hinges in the cylindrical structure. The ductile hinges 20 are stress/strain concentration features designed to operate into the plastic deformation range of generally ductile materials. Such features are also commonly referred to as "Notch Hinges" or "Notch Springs" in ultra-precision mechanism design, where they are used exclusively in the elastic range.

Although the elongated struts 18 have been shown as L-shaped, other shaped struts may also be used as long as the struts are connected to the ductile hinges 20 and the bridging elements 18 with the same spatial arrangement. For example, struts having J-shapes or amorphous shapes may also be used.

With reference to the drawings and the discussion, the width of any feature is defined as its dimension in the circumferential direction of the cylinder. The length of any feature is defined as its dimension in the axial direction of the cylinder. The thickness of any feature is defined as the wall thickness of the cylinder.

The ductile hinges 20 may be symmetrical or asymmetric ductile hinges. The ductile hinges 20 essentially take the form of a small, prismatic strut having a substantially constant cross section or a tapering cross section, as will be discussed below. As the cylindrical tubes 12 are expanded, bending or plastic deformation occurs in the ductile hinges 20, and the elongated struts 18 are not plastically deformed.

The presence of the ductile hinges 20 allows all of the remaining features in the tissue supporting device 10 to be increased in width or the circumferentially oriented component of their respective rectangular moments of inertia—thus greatly increasing the strength and rigidity of these features. The net result is that elastic, and then plastic deformation commence and propagate in the ductile hinges 20 before other structural elements of the device undergo any significant elastic deformation. The force required to expand the tissue supporting device 10 becomes a function of the geometry of the ductile hinges 20, rather than the device structure as a whole, and arbitrarily small expansion forces can be specified by changing hinge geometry for virtually any material wall thickness. The ability to increase the width and thickness of the elongated struts 18 provides additional area and depth for providing beneficial agent openings 30 containing a beneficial agent for delivery to the tissue.

In the preferred embodiment of FIG. 2, it is desirable to increase the width of the individual struts 18 between the ductile hinges 20 to the maximum width that is geometrically possible for a given diameter and a given number of struts arrayed around that diameter. The only geometric limitation on strut width is the minimum practical width of the slots 16 which is about 0.002 inches (0.0508 mm) for laser machining. Lateral stiffness of the struts 18 increases as the cube of strut width, so that relatively small increases in strut width significantly increase strut stiffness. The net result of inserting ductile hinges 20 and increasing strut width is that the struts 18 no longer act as flexible leaf springs, but act as essentially rigid struts between the ductile hinges. All radial expansion or compression of the cylindrical tissue supporting device 10 is accommodated by mechanical strain in the hinge features 20, and yield in the hinge commences at very small overall radial expansion or compression.

The ductile hinge 20 illustrated in FIG. 2 is exemplary of a preferred structure that will function as a stress/strain concentrator. Many other stress/strain concentrator configurations may also be used as the ductile hinges in the present invention, as shown and described by way of example in U.S. Pat. No. 6,241,762, the entire contents of which is hereby incorporated by reference. The geometric details of the stress/strain concentration features or ductile hinges 20 can be varied greatly to tailor the exact mechanical expansion properties to those required in a specific application.

Figure 4:
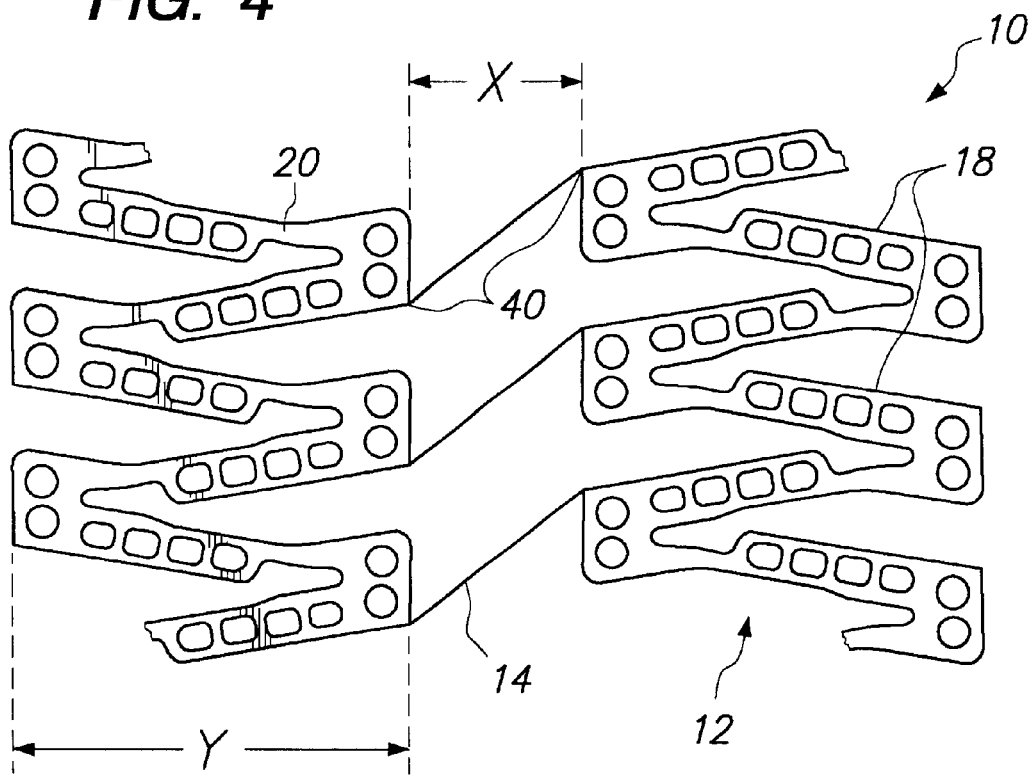
FIG. 4 is a schematic side view of a portion of the device of FIG. 2 in a partially expanded configuration.
Figure 5:
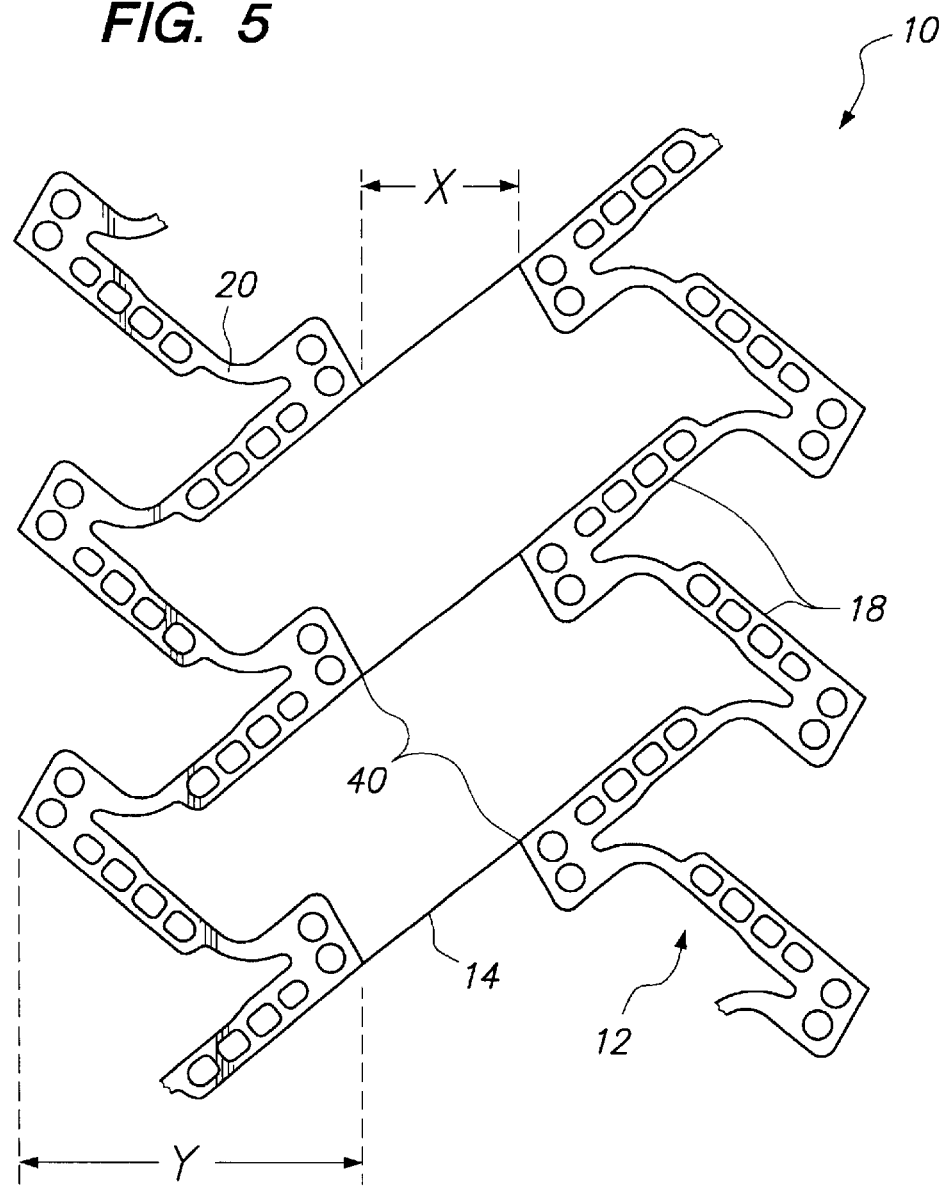
FIG. 5 is a schematic side view of a portion of the device of FIG. 2 in a fully expanded configuration.
Figure 6:
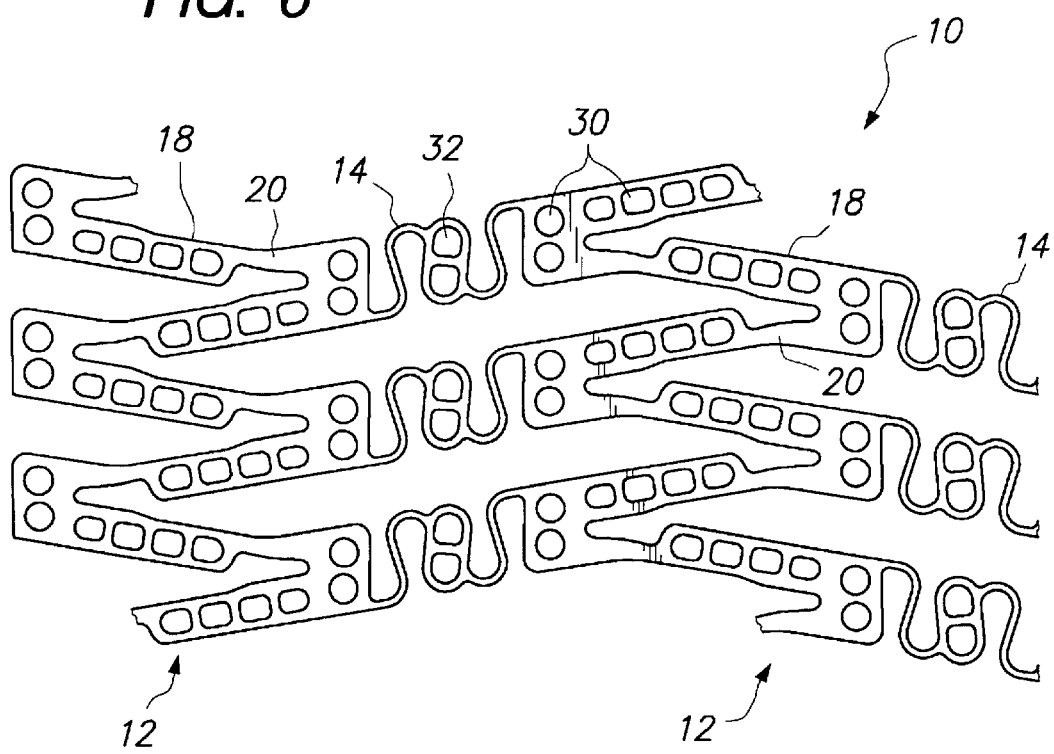
FIG. 6 is an enlarged side view of a portion of a tissue supporting device in a partially expanded configuration.

As shown in FIGS. 2–6, at least one and more preferably a series of openings 30 are formed by laser drilling or any other means known to one skilled in the art at intervals along a neutral axis of the struts 18. Similarly, at least one and preferably a series of openings 32 are formed at selected locations in the bridging elements 14, as shown in FIG. 6. Although the use of openings 30, 32 in both the struts 18 and bridging elements 14 is preferred, it should be clear to one skilled in the art that openings could be formed in only one of the struts and bridging elements. In the illustrated embodiment, the openings 30, 32 are circular, rectangular, and polygonal in nature and form openings extending through the width of the tissue supporting device 10. It should be apparent to one skilled in the art, however, that openings of any geometrical shape or configuration could of course be used without departing from the scope of the present invention. In addition, the openings 30, 32 may be in the form of recesses having a depth less than the thickness of the device.

The behavior of the struts 18 in bending is analogous to the behavior of an I-beam or truss. The outer edges of the struts 18 correspond to the I-beam flange and carry the tensile and compressive stresses, whereas the inner edges of the struts 18 correspond to the web of an I-beam which carries the shear and helps to prevent buckling and wrinkling of the faces. Since most of the bending load is carried by the outer edges of the struts 18, a concentration of as much material as possible away from the neutral axis results in the most efficient sections for resisting strut flexure. As a result, material can be judiciously removed along the axis of the strut so as to form openings 30 without adversely impacting the strength and rigidity of the strut. Since the struts 18 and portions of the bridging elements 14 containing openings remain essentially rigid during stent expansion, the openings 30, 32 are also non-deforming.

The openings 30, 32 in the struts 18 and the bridging elements 14 may promote the healing of the intervention site by promoting regrowth of the endothelial cells. By providing the openings 30, 32 in the struts 18 and the bridging elements 14, the cross section of the strut is effectively reduced without decreasing the strength and integrity of the strut, as described above. As a result, the overall distance across which endothelial cell regrowth must occur is also reduced to approximately 0.0025–0.0035 inches, which is approximately one-half of the thickness of a conventional stent. It is further believed that during insertion of the expandable medical device, cells from the endothelial layer may be scraped from the inner wall of the lumen by the openings 30, 32 and remain therein after implantation. The presence of such endothelial cells would thus provide a basis for the healing of the lumen.

At least some of the openings 30, 32 are preferably loaded with an agent, most preferably a beneficial agent, for delivery to the lumen in which the tissue support device 10 is deployed.

The terms "agent" or "beneficial agent" as used herein are intended to have the broadest possible interpretation and are used to include any therapeutic agent or drug, as well as inactive agents such as barrier layers or carrier layers. The terms "drug" and "therapeutic agent" are used interchangeably to refer to any therapeutically active substance that is delivered to a bodily lumen of a living being to produce a desired, usually beneficial, effect. The present invention is particularly well suited for the delivery of antiproliferatives (anti-restenosis agents) such as paclitaxel and rapamycin for example, and antithrombins such as heparin, for example. The beneficial agent includes classical small molecular weight therapeutic agents commonly referred to as drugs including all classes of action as exemplified by, but not limited to: antiproliferatives, antithrombins, antiplatelet, antilipid, anti-inflammatory, and anti-angiogenic, vitamins, ACE inhibitors, vasoactive substances, antimitotics, metello-proteinase inhibitors, NO donors, estradiols, and anti-sclerosing agents, alone or in combination. Beneficial agent also includes larger molecular weight substances with drug like effects on target tissue sometimes called biologic agents including but not limited to: peptides, lipids, protein drugs, enzymes, oligonucleotides, ribozymes, genetic material, prions, virus, bacteria, and eucaryotic cells such as endothelial cells, monocyte/macrophages or vascular smooth muscle cells to name but a few examples. Other beneficial agents may include but not be limited to physical agents such as microspheres, microbubbles, liposomes, radioactive isotopes, or agents activated by some other form of energy such as light or ultrasonic energy, or by other circulating molecules that can be systemically administered.

The embodiment of the invention shown in FIG. 2 can be further refined by using Finite Element Analysis and other techniques to optimize the deployment of the beneficial agent within the openings of the struts 18 and bridging elements 14. Basically, the shape and location of the openings 30, 32 can be modified to maximize the volume of the voids while preserving the relatively high strength and rigidity of the struts 18 with respect to the ductile hinges 20. According to one preferred embodiment of the present invention, the openings have an area of at least $5 \times 10^{-6}$ square inches, and preferably at least $7 \times 10^{-6}$ square inches.

Examples of the ways in which the agent may be loaded in the openings 30, 32 are described in U.S. Provisional Patent Application Serial No. 60/314,259, filed Aug. 20, 2001, and U.S. patent application Ser. No. 09/948,989, filed on Sep. 7, 2001, both of which are incorporated herein by reference.

Figure 1:
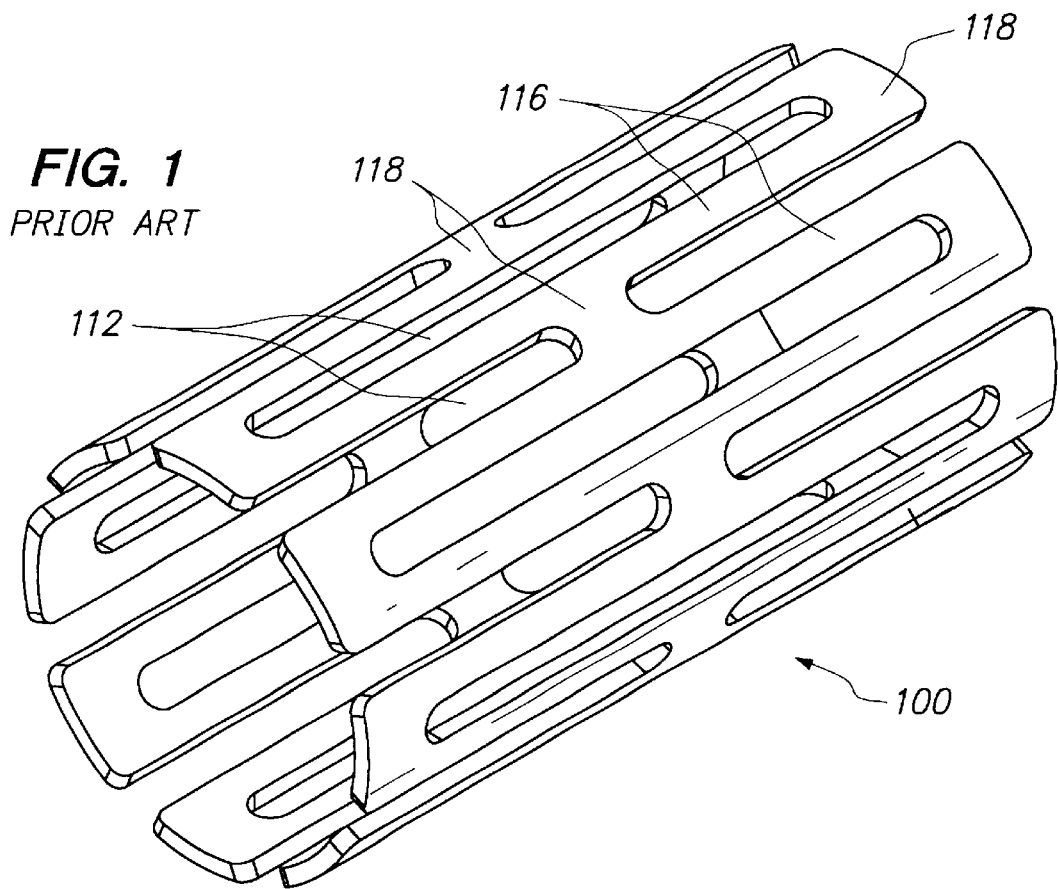
FIG. 1 is an isometric view of a prior art tissue-supporting device.

FIG. 1 shows a typical prior art "expanding cage" stent design. The stent 110 includes a series of axial slots 112 formed in a cylindrical tube. Each axial row of slots 112 is displaced axially from the adjacent row by approximately half the slot length providing a staggered slot arrangement. The material between the slots 112 forms a network of axial struts 116 joined by short circumferential links 118.

The known prior art stents, as shown in FIG. 1 as well as the stents of U.S. Pat. No. 6,241,762 expand into roughly diamond or hexagonal shaped cells. As described above, a measure of the distance from the stent elements or struts to the most distant tissue portions is the diameter of the inscribed circle which can be drawn between expanded stent elements. The size of the inscribed circles is similar for the stents having diamond or hexagonal shaped cells, given equal coverage ratios. The coverage ratio is defined as the ratio of the stent surface area to the area of the lumen in which the stent is deployed. Clinically preferred coverage ratios are in the about 12% to about 20% range.

Figure 3:
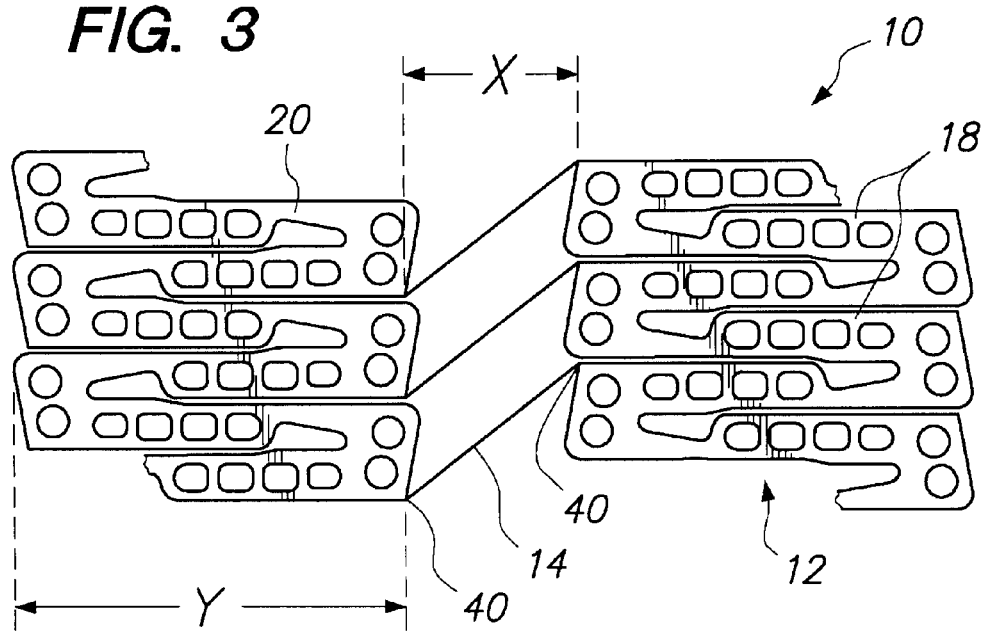
FIG. 3 is a schematic side view of a portion of the device of FIG. 2 in an unexpanded configuration.

FIGS. 2–5 illustrate one example of an embodiment of the present invention that improves the spatial distribution of the beneficial agent. FIG. 5 shows an enlarged side view of this embodiment after device expansion. The shape of the cells bordered by the stent struts 18 and bridging elements 14 in this embodiment may be described as helically oriented parallelograms. The adjacent struts 18 form rows of alternately oriented "chevrons" or V-shapes when expanded. It can be shown that the inscribed circle for this arrangement is approximately 40% smaller than inscribed circles for the diamond or hexagonal cells of the stents mentioned above, for similar coverage ratios. Thus, the parallelogram shaped expanded cell structure provides a very substantial improvement in the spatial distribution of the beneficial agent delivered by the struts 18 and bridging elements 14.

Further, this improved spatial distribution can be accomplished without the longitudinal contraction of the beneficial agent bearing struts 18, and the corresponding longitudinal expansion of agent-poor bridging elements 14, that characterizes the stents of U.S. Pat. No. 5,843,120. The improved spatial distribution of the struts achieves improved spatial distribution of beneficial agent whether the agent is provided in the opening, in a coating, in both openings and a coating, or otherwise loaded in or on the device.

As shown in FIG. 2, it can be seen that a single ductile hinge 20 is located at alternating ends of adjoining L-shaped struts 18. The center of rotation between any pair of adjoining struts 18 is thus displaced from the axis bisecting the strut pair, and strut motion during expansion is more complex than that of the double hinged struts described in U.S. Pat. No. 6,241,762. Basically, the L-shape struts 18 on either side of a given ductile hinge 20 can be seen as rotating about an instant center that moves along a (circumferentially oriented) perpendicular bisector of the ductile hinge element. It should be noted that while a ductile hinge 20 is the preferred method for accomplishing this motion, any method which provided a pivoting action between adjoining L-shaped elements would be within the scope of this invention.

Figure 7:
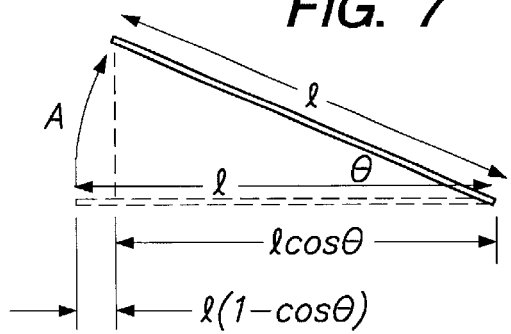
FIG. 7 is a diagram of the change in longitudinal length of the long leg of the L-shaped strut element during radial expansion.
Figure 8:
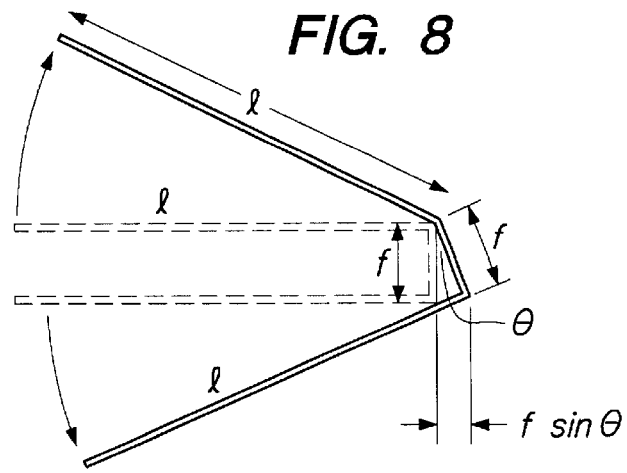
FIG. 8 is a diagram of the change in longitudinal length of the short leg of the L-shaped strut element during radial expansion.

A simplified geometrical analysis of this motion of the struts upon stent expansion may be made with respect to FIGS. 7 and 8. Here l is the horizontal length of the L-shaped strut 18 or the length of the long leg 22 and f is the offset between the bottom of the strut and the instant center of rotation or roughly the length of the shorter leg 24 of the L-shaped strut 18. The initial position of the instant center is selected by specifying the initial position and curvature of the ductile hinge 20 and the circumferential width of the strut 18. As the device expands, the long leg rotates away from the horizontal axis as shown by the arrow A in FIG. 7, and the longitudinal component of long leg 22 of the strut 18 is decreased by the amount $l(1-\cos\theta)$. Simultaneously, however, this length contraction is offset by the rotation of the vertical element for the short leg 24. As shown in FIG. 8, the increase in the longitudinal component of the short leg 24 can be expressed as $f(\sin\theta)$. For smaller values of $\theta$, $f(\sin\theta)$ changes more rapidly than $l(1-\cos\theta)$, with the result that the ratios of l to f or the ratios of the lengths of the long and short legs can be manipulated to give a net change of zero in the longitudinal extent of the strut pair over a range of angles, but generally less than about 40°. This ratio can be expressed as:

$$\frac{l}{f} = \frac{(\sin \theta)}{(1 - \cos \theta)}$$

For example, an expansion angle of 37° and an l/f ratio of 2.99 would result in net longitudinal contraction of zero. A preferred ratio of the length of the long leg 22 to the length of the short leg is about 2:1 to about 6:1.

Further advantage can be made of this zero contraction geometry by inverting the orientation of ductile hinges in adjacent groups of struts, as shown in the expansion sequence of FIGS. 3–5. In this "counter rotating" configuration, unique pairs of points can be identified on adjacent strut groups (adjacent cylinders 12) for which the total distance between the point pairs remains essentially constant throughout the device expansion sequence. If the struts 18 are connected to the bridging elements 14 at these connecting points 40, the entire device deployment sequence can be thought of as the rotation of all the interconnected strut 18 and bridging elements 14 about these connecting points 40. Since only rotation, and not expansion is now required of the bridging elements 14, the bridging elements themselves may be modified to include inflexible elements (small struts) that may contain additional beneficial-agent bearing reservoirs or openings 32, thus further improving the uniformity of beneficial agent delivery.

As shown in the expansion sequence of FIGS. 3–5, a longitudinal distance X between the connecting points 40 on opposite ends of the bridging elements 14 or between the cylindrical tubes 12 remains substantially constant during expansion of the device 10. In addition, the longitudinal length Y of the cylindrical tubes 12 also remains substantially constant during radial expansion.

The design criteria of ductile hinges for the preferred embodiments described above is different for the ductile hinges in the stents described in U.S. Pat. No. 6,241,762. Since the total number of ductile hinges 20 in the present embodiment is generally reduced by half over those in U.S. Pat. No. 6,241,762, while the total deflection to be accommodated by the hinges remains the same, the length of individual hinges must generally be increased to keep material strains within acceptable limits. If the width of the hinge is kept constant along the axis of the hinge over this increased length, bending stresses and strains are not evenly distributed through the hinge and bending is not uniform.

Figure 9:
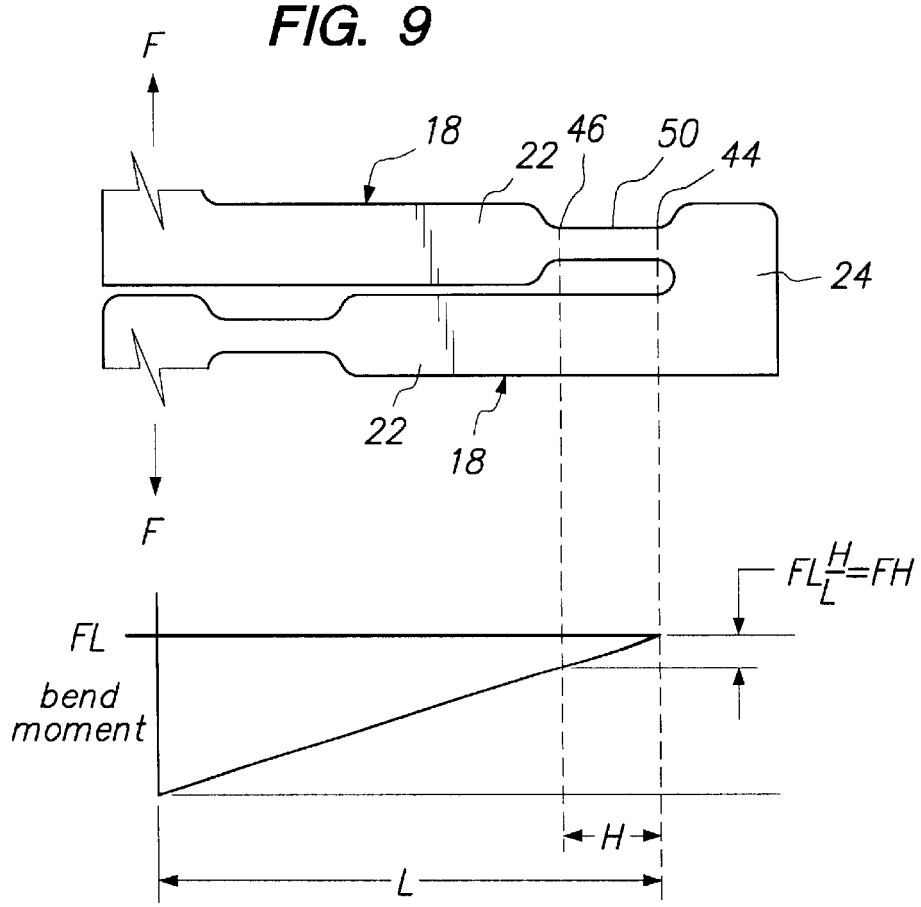
FIG. 9 is a simple moment diagram showing the variation in a bend moment along the horizontal axis of a strut and ductile hinge.
Figure 10:
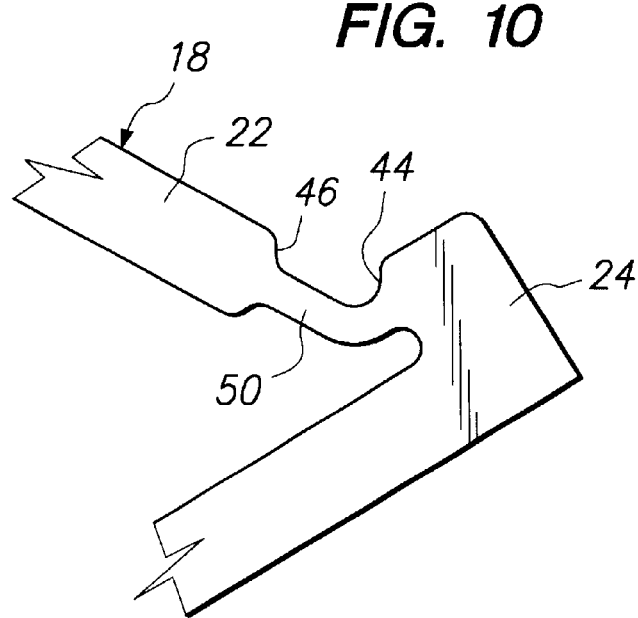
FIG. 10 is an enlarged side view of a portion of an expanded device according to the present invention having a constant width ductile hinge.

FIG. 9 shows two struts 18 of the present invention joined by a ductile hinge 50, with a simple moment diagram showing the variation in bend moment along the horizontal axis of the strut 18 and the ductile hinge 50 as bending in the hinge commences by application of the forces F. It can be seen that the bend moment applied to the hinge 50 increases linearly from left to right. The hinge develops significant curvature as the device expands, with the result that the hinge is subjected to a complex array of stresses comprising significant axial, shear, and bending stress components. These stresses vary in both magnitude and direction as a function of hinge curvature. In general, bend moment will increase toward a hinge end 44 connected to the short leg 24 at all curvatures, while applied axial forces (i.e., the component of applied forces aligned with the hinge axis) will increase toward the hinge end 46 connected to the long leg 22. The result for a long hinge 50 of constant cross section is illustrated in FIG. 10, wherein it can be seen that strain and peak stresses, and thus curvature, are concentrated in region close to the hinge end 44, rather than uniformly distributed along the entire length of the hinge.

Figure 11:
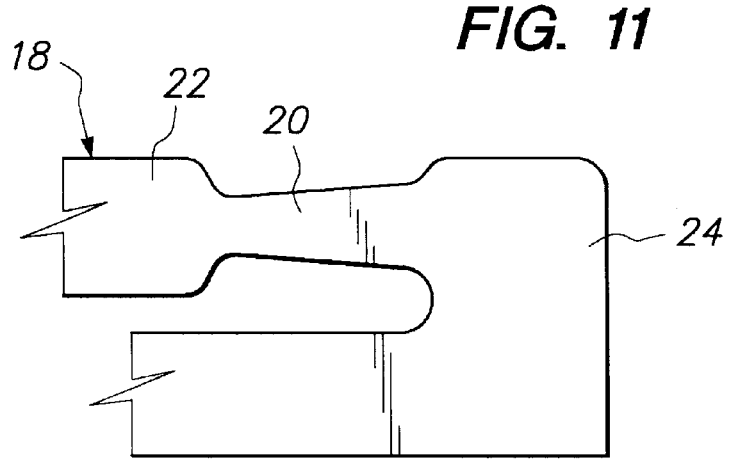
FIG. 11 is an enlarged side view of a portion of an unexpanded device according to the present invention having a tapered ductile hinge.

One efficient hinge design for use in the present invention is one in which the hinge is uniformly strained along its entire axis. For the array of applied stresses outlined above, this can be achieved by varying the width of the hinge gradually along its axis to match the plastic moment of the hinge to the applied stresses at each hinge cross section. FIG. 11 shows a straight tapered ductile hinge 20 in which the hinge width is increased from left to right or from the end adjacent the long leg 22 to the end adjacent the short leg 24 of the strut 18, in a linear fashion. In a typical embodiment, a 0.010 inch long hinge might taper from about 0.0050 inch maximum width to about 0.0035 inch minimum width from one end to the other, resulting in a hinge taper of about 0.15 inches per inch. Preferred embodiments will generally have tapers ranging from about 0.1 to about 0.2 inches per inch.

Finite Element Analysis can be used to create optimized, non-linear tapers for specific strut/hinge geometries. For example, hinges may be created with an initial curvature, as described in U.S. Pat. No. 6,241,762 for certain applications. In this case, a hinge would be bounded by two curves, creating a non-linear taper, which would nevertheless fall within the same range of overall taper ratios described above.

While the invention has been described in detail with reference to the preferred embodiments thereof, it will be apparent to one skilled in the art that various changes and modifications can be made and equivalents employed, without departing from the present invention.

What is claimed is:

1. An expandable medical device comprising:

a plurality of elongated struts, the plurality of elongated struts joined together to form a substantially cylindrical device which is expandable from a cylinder having a first diameter to a cylinder having a second diameter, wherein adjacent ones of the plurality of elongated struts are substantially parallel when the cylinder is at the first diameter and the adjacent elongated struts form V-shapes when the cylinder is at the second diameter; and a plurality of pivots joining the plurality of struts together in the substantially cylindrical device, wherein only one pivot interconnects each two adjacent elongated struts and the pivots are each located offset from a line bisecting the V-shapes formed by the elongated struts when the cylinder is at the second diameter.

2. The device of claim 1, wherein the elongated struts are substantially L-shaped struts and the plurality of pivots connect an end of a short leg of the L-shaped strut to an end of a long leg of an adjacent L-shaped strut.

3. The device of claim 2, wherein an orientation of every other adjacent L-shaped strut is inverted with respect to the remaining L-shaped struts.

4. The device of claim 2, wherein the L-shaped struts are nested and the long legs of the L-shaped struts are substantially parallel when the cylinder is at the first diameter.

5. The device of claim 1, wherein the plurality of pivots are ductile hinges and wherein a width of the ductile hinges is smaller than a width of the elongated struts.

6. The device of claim 5, wherein the ductile hinges are tapered.

7. The device of claim 5, wherein the ductile hinges have a taper of about 0.1 to about 0.2 inches per inch.

8. The device of claim 1, wherein the plurality of pivots join radially adjacent struts together, and the pivots are each located offset from the line bisecting the V-shapes formed by the radially adjacent struts.

9. An expandable medical device comprising:
a plurality of elongated struts, the plurality of elongated struts joined together to form a substantially cylindrical device which is expandable from a cylinder having a first diameter to a cylinder having a second diameter, wherein adjacent ones of the plurality of elongated struts are substantially parallel when the cylinder is at the first diameter and the adjacent elongated struts form V-shapes when the cylinder is at the second diameter; and
a plurality of ductile hinges connecting the plurality of struts together in the substantially cylindrical device, wherein only one ductile hinge interconnects each two adjacent elongated struts and the ductile hinges are each located offset from a line bisecting the V-shapes formed by the elongated struts when the cylinder is at the second diameter, the ductile hinges having a hinge width which is smaller than a strut width such that as the device is expanded from the first diameter to the second diameter the ductile hinges experience plastic deformation while the struts are not plastically deformed.

10. The device of claim 9, wherein the elongated struts are substantially L-shaped struts and the plurality of ductile hinges connect an end of a short leg of the L-shaped strut to an end of a long leg of an adjacent L-shaped strut.

11. The device of claim 10, wherein an orientation of every other adjacent L-shaped strut is inverted with respect to the remaining L-shaped struts.

12. The device of claim 10, wherein the L-shaped struts are nested and the long legs of the L-shaped struts are substantially parallel when the cylinder is at the first diameter.

13. The device of claim 10, wherein the ductile hinges are tapered.

14. The device of claim 9, wherein the plurality of ductile hinges join radially adjacent struts together.

15. An expandable medical device comprising:
a plurality of struts each having a long leg, a short leg connected to the long leg, and a connecting point, wherein the long leg has a length longer than a length of the short leg;
a plurality of pivots joining the long leg of one strut to the short leg of an adjacent strut to form a substantially cylindrical device which is expandable from a cylinder having a first diameter to a cylinder having a second diameter, wherein as the substantially cylindrical device is expanded from the first diameter to the second diameter the pivots bend; and
a plurality of bridging members connected to the connecting points of struts in one row and to the connecting points of struts in an adjacent row to form an expandable device configured such that a total length of the bridging members remains substantially constant during radial expansion.

16. The device of claim 15, wherein portions of the plurality of bridging members are configured to remain substantially parallel during expansion.

17. The device of claim 15, wherein the plurality of cylindrical members further comprise a beneficial agent for delivery to tissue.

18. The device of claim 15, wherein the expandable device is configured for radial expansion while an overall length of the device remains substantially constant.

19. The device of claim 15, wherein the total length of the bridging members is measured in an axial direction of the substantially cylindrical device.

20. An expandable medical device comprising:
a plurality of elongated struts, the plurality of elongated struts joined together by pivoting connections to form a substantially cylindrical device which is expandable from a cylinder having a first diameter to a cylinder having a second diameter, wherein adjacent ones of the plurality of elongated struts are substantially parallel when the cylinder is at the first diameter and the adjacent elongated struts form a plurality of substantially parallelogram shapes when the cylinder is at the second diameter, the substantially parallelogram shapes having first and second opposite sides which are longer than third and fourth opposite sides.

21. The device of claim 20, wherein a beneficial agent is affixed in a plurality of openings formed in the plurality of elongated struts.

22. The device of claim 20, wherein a beneficial agent is coated on the plurality of struts.

23. The device of claim 20, wherein the plurality of elongated struts are arranged to form a plurality of chevrons having alternating orientations.

24. The device of claim 20, wherein the plurality of elongated struts are interconnected with bridging elements to form the substantially parallelogram shapes.

25. An expandable medical device for delivery of a beneficial agent, the device comprising:
a plurality of elongated struts, the plurality of elongated struts joined together by pivoting connections to form a substantially cylindrical device which is expandable from a cylinder having a first diameter to a cylinder having a second diameter, wherein adjacent ones of the plurality of elongated struts are substantially parallel when the cylinder is at the first diameter and the adjacent elongated struts form a plurality of substantially parallelogram shapes when the cylinder is at the second diameter, the substantially parallelogram shapes having first and second opposite sides which are longer than third and fourth opposite sides;
a beneficial agent affixed to the plurality of struts for delivery to tissue.

26. The device of claim 25, wherein the beneficial agent is affixed in a plurality of openings formed in the plurality of elongated struts.

27. The device of claim 25, wherein the beneficial agent is coated on the plurality of struts.

28. The device of claim 25, wherein the plurality of elongated struts are arranged to form a plurality of chevrons having alternating orientations.

29. The device of claim 25, wherein the plurality of elongated struts are interconnected with bridging elements to form the substantially parallelogram shapes.

30. The device of claim 25, wherein the expandable medical device has a coverage ratio of about 12% to about 20%.

31. The device of claim 25, wherein the beneficial agent is paclitaxel, or an analogue or derivative thereof.

32. The device of claim 25, wherein the beneficial agent is rapamycin, or an analogue or derivative thereof.

33. An expandable medical device comprising:
a plurality of elongated struts;
a plurality of ductile hinges connecting the plurality of struts together in a substantially cylindrical medical device which is expandable from a cylinder having a first diameter to a cylinder having a second diameter, wherein the plurality of ductile hinges are tapered with the taper oriented to achieve uniform strain along the ductile hinge during expansion of the cylinder from the first diameter to the second diameter.

34. The device of claim 33, wherein adjacent elongated struts form V-shapes when the cylinder is at the second diameter and wherein the plurality of ductile hinges are each tapered such that an end of the ductile hinge closer to the apex of the V-shape formed by the adjacent elongated struts has a width which is greater than a width of the ductile hinge at an opposite end.

35. The device of claim 33, wherein the taper of the ductile hinges is about 0.1 to about 0.2 inches per inch.

36. The device of claim 33, wherein the taper of the ductile hinges is about 0.2 inches per inch or less.

37. The device of claim 36, wherein the taper is substantially constant along a length of the ductile hinges.

38. The device of claim 33, wherein the taper is a non-linear taper bounded by two curves.

39. The device of claim 33, wherein the ductile hinge has a largest cross sectional area at a point where stresses in the beam are greatest during expansion from the first diameter to the second diameter.

40. The device of claim 33, wherein the taper extends along substantially an entire length of the ductile hinges.

* * * * *